United States Patent [19]
Chanoch

[11] Patent Number: 5,688,251
[45] Date of Patent: Nov. 18, 1997

[54] CARTRIDGE LOADING AND PRIMING MECHANISM FOR A PEN INJECTOR

[75] Inventor: Lawrence H. Chanoch, Mahwah, N.J.

[73] Assignee: Becton Dickinson and Company, Franklin Lakes, N.J.

[21] Appl. No.: 530,527

[22] Filed: Sep. 19, 1995

[51] Int. Cl.⁶ .................................................. A61M 5/00
[52] U.S. Cl. ............................. 604/208; 604/186; 604/187; 604/232; 222/46; 222/309
[58] Field of Search ...................... 604/110, 186, 604/187, 188, 192, 195, 196, 221, 207–211, 232, 71, 72, 218, 224, 234; 222/46, 48, 309

[56] References Cited

U.S. PATENT DOCUMENTS

| | | | |
|---|---|---|---|
| 4,592,745 | 6/1986 | Rex et al. | 604/211 |
| 4,865,591 | 9/1989 | Sams | 604/186 |
| 4,936,833 | 6/1990 | Sams | 604/232 |
| 5,112,317 | 5/1992 | Michel | 604/208 |
| 5,226,895 | 7/1993 | Harris | 604/208 |
| 5,279,585 | 1/1994 | Balkwill | 604/207 |
| 5,304,152 | 4/1994 | Sams | 604/207 |
| 5,383,865 | 1/1995 | Michel | 604/232 |

Primary Examiner—Corrine M. McDermott
Assistant Examiner—Cris L. Rodriguez
Attorney, Agent, or Firm—Alan W. Fiedler

[57] ABSTRACT

A medication delivery pen is provided having a medication cartridge holder assembly, a pen body assembly and a cap. The reusable pen body assembly includes an improved loading and priming mechanism that allows the user to easily load a new cartridge and prime the pen without having to manually manipulate the pen's lead screw and related driving components.

9 Claims, 5 Drawing Sheets

CARTRIDGE LOADING AND PRIMING MECHANISM FOR A PEN INJECTOR

BACKGROUND OF THE INVENTION

1. Field of the Invention

The subject invention relates to an improved cartridge loading and priming mechanism for a medication delivery pen having a cartridge holder assembly and a pen body assembly removably mounted to the cartridge holder assembly for delivering selected doses of medication.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal and accessed by piercing the elastomeric seal with the needle cannula. A selected dose of the medication may be drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the typical hypodermic syringe and separate medication vial. However, the disassembly of the pen to remove empty medication vials and to insert new ones is an inconvenience. As a result, disposable pens have been developed. The prior art disposable medication delivery pen includes a vial of insulin or other such medication permanently encapsulated therein. The patient need merely connect a double-ended needle cannula to the disposable pen for each administration of medication. The prior art disposable pen can be discarded when the supply of medication permanently encapsulated therein has been exhausted.

Disposable medication delivery pens offer certain conveniences to the patient who is required to self-administer medication. However, the dose selecting and driving mechanisms of prior art medication delivery pens are fairy complex devices and costly to manufacture. Hence, a substantial cost penalty is associated with the convenience of using a disposable medication delivery pen.

Another problem with the above-described medication delivery pens is in loading and priming the penis. These pens usually utilize a lead screw and matching nut combination that translate a rotary dose setting motion into a linear lead screw motion required to expel medication from the pen or cartridge. In such a mechanism, the nut is allowed to rotate during medication delivery while rotation of the lead screw is prevented by means of a rigidly mounted ring with tabs extending into the lead screw. Therefore, as the nut turns the pre-selected amount, threads on the nut and lead screw cause the lead screw to move axially to deliver the medication. Then, when the cartridge is empty and must be replaced, the fully extended lead screw must be manually rotated and returned to a starting position to receive a new cartridge. However, manual rotation of the lead screw is very difficult since the tabbed ring is intended to prevent rotation of the lead screw.

SUMMARY OF THE INVENTION

It is an objective of the present invention to overcome the problem with moving the lead screw back into the pen during cartridge loading found in prior art pens by providing a medication delivery pen having an improved cartridge loading and priming mechanism that allows a patient to easily load and prime the pen. The present invention provides a pen with a lead screw that is easily slid back into the pen during cartridge loading and thereby eliminates the need for a patient to manipulate an anti-rotation tabbed ring. In the present invention the lead screw does not stop sliding until the cartridge holder assembly has been fully threaded onto the pen housing and, therefore, provides automatic priming of the pen during the threading operation and causes the lead screw to automatically engage with a drive mechanism.

In particular, the medication delivery pen of the present invention includes a medication cartridge holder assembly that is selectively engageable with and disengageable from a pen body assembly. In particular, the medication delivery pen includes means for allowing the lead screw in the medication delivery pen to automatically and easily slide into and prime the medication delivery pen as the cartridge assembly approaches the pen body assembly, when the lead screw is in contact with the plunger in the cartridge. The medication pen also includes means for engaging the lead screw to the cartridge holder assembly as the cartridge is being threaded to the pen body assembly and means for engaging the lead screw to the drive mechanism when the cartridge holder assembly has been fully threaded to the pen body assembly.

These and other aspects, features and advantages of the present invention will become apparent from the following detailed description taken in conjunction with the accompanying drawings.

DETAILED DESCRIPTION

A medication delivery pen in accordance with the subject invention is identified generally by the numeral 10 in FIGS. 1–4. Medication delivery pen 10, as shown in FIGS. 1–4, includes a reusable pen body assembly 100, a cap 200, a cartridge holder assembly 300, and a needle cannula assembly 500. Cartridge holder assembly 300 includes opposed proximal and distal ends 301 and 302, respectively. Proximal end 301 of cartridge holder assembly 300 is dimensioned and configured to threadedly engage pen body assembly 100, as explained further herein. Distal end 302 of cartridge holder assembly 300 is configured to securely but releasably engage needle cannula assembly 500.

Figure 1:
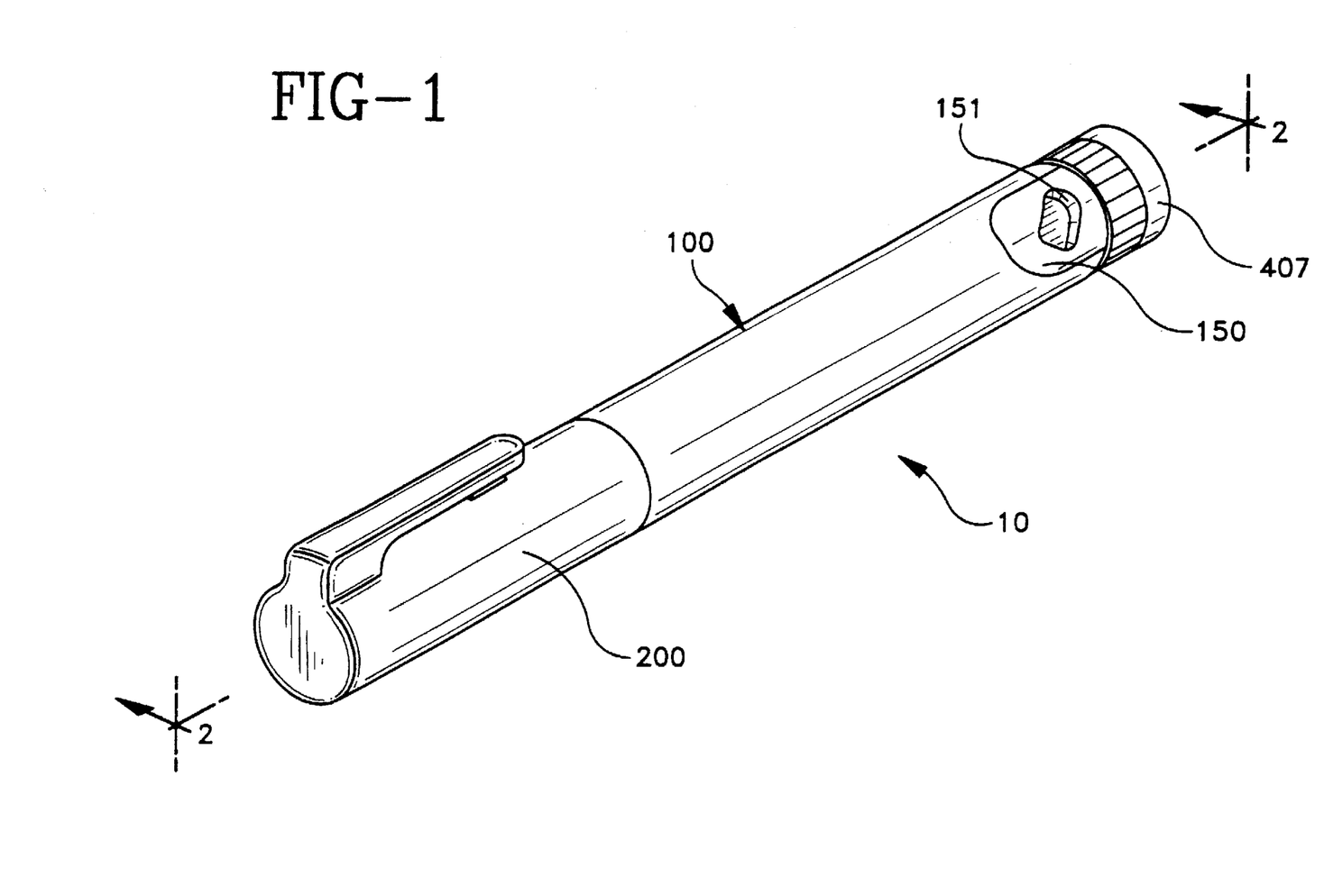
FIG. 1 is a perspective view of the medication delivery pen of the subject invention.
Figure 2:
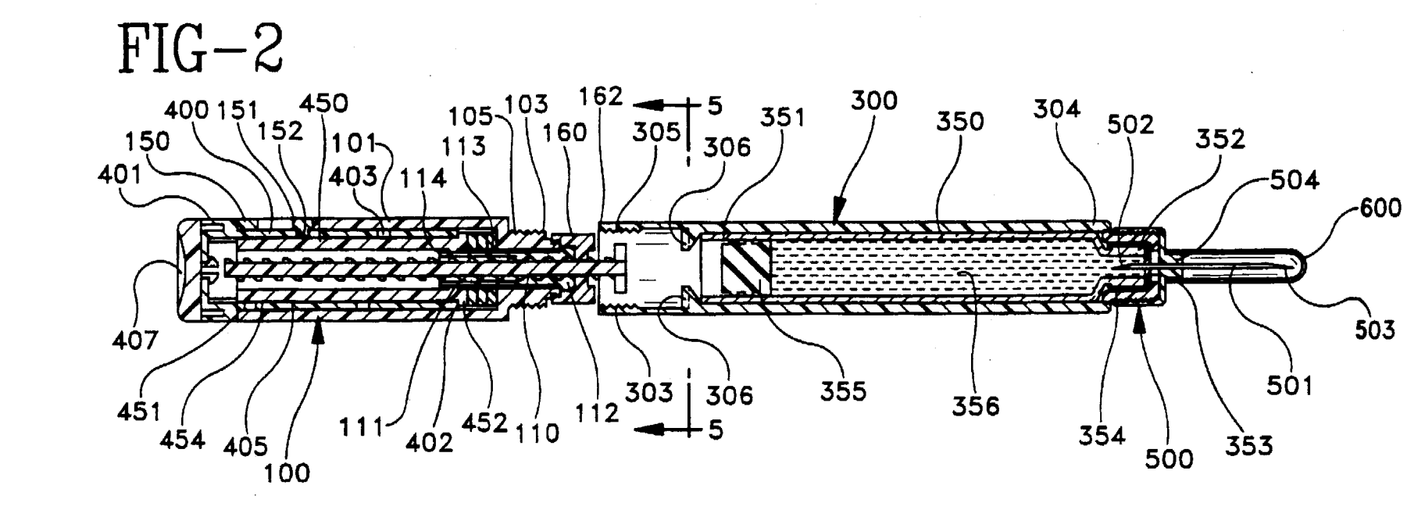
FIG. 2 is a longitudinal cross-sectional view of an unassembled medication delivery pen shown in FIG. 1 along lines 2—2.
Figure 3:
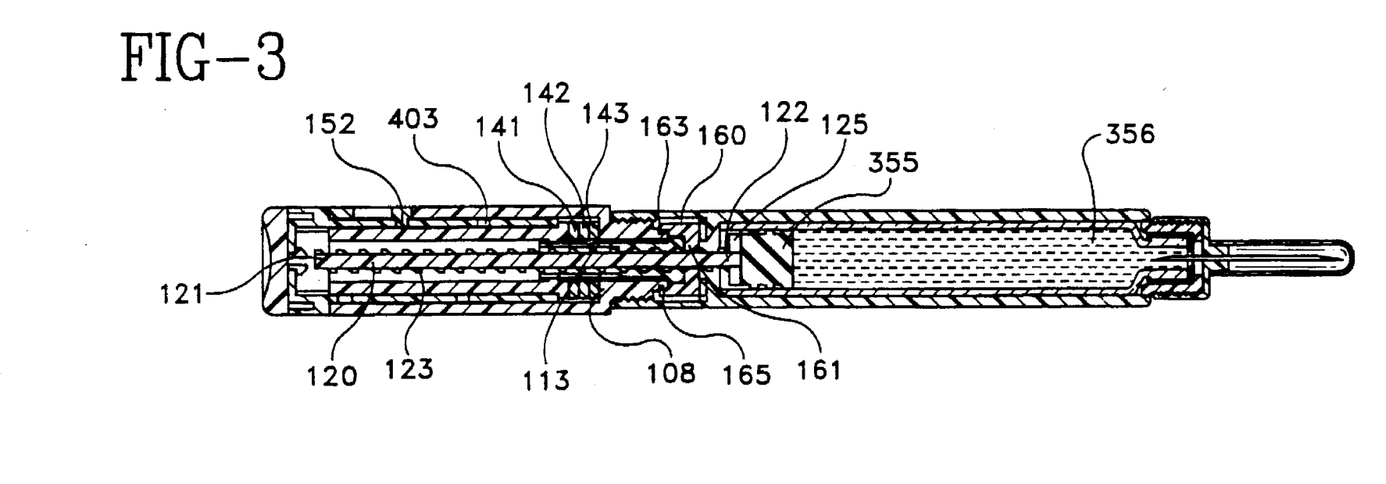
FIG. 3 is a longitudinal cross-sectional view of an assembled medication delivery pen shown in FIG. 2.
Figure 4:
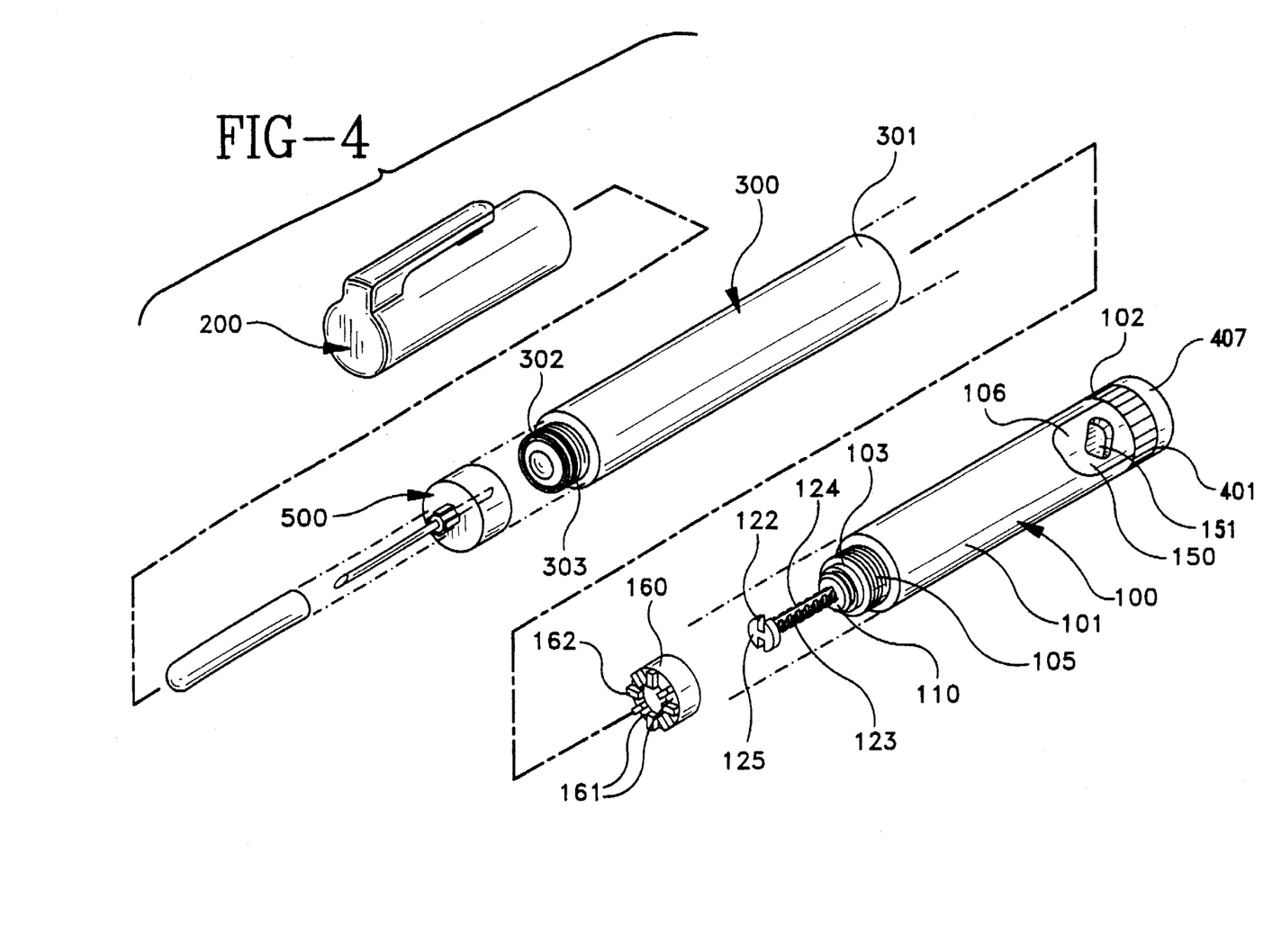
FIG. 4 is a exploded perspective view of the medication delivery pen shown in FIG. 1.
Figure 5:
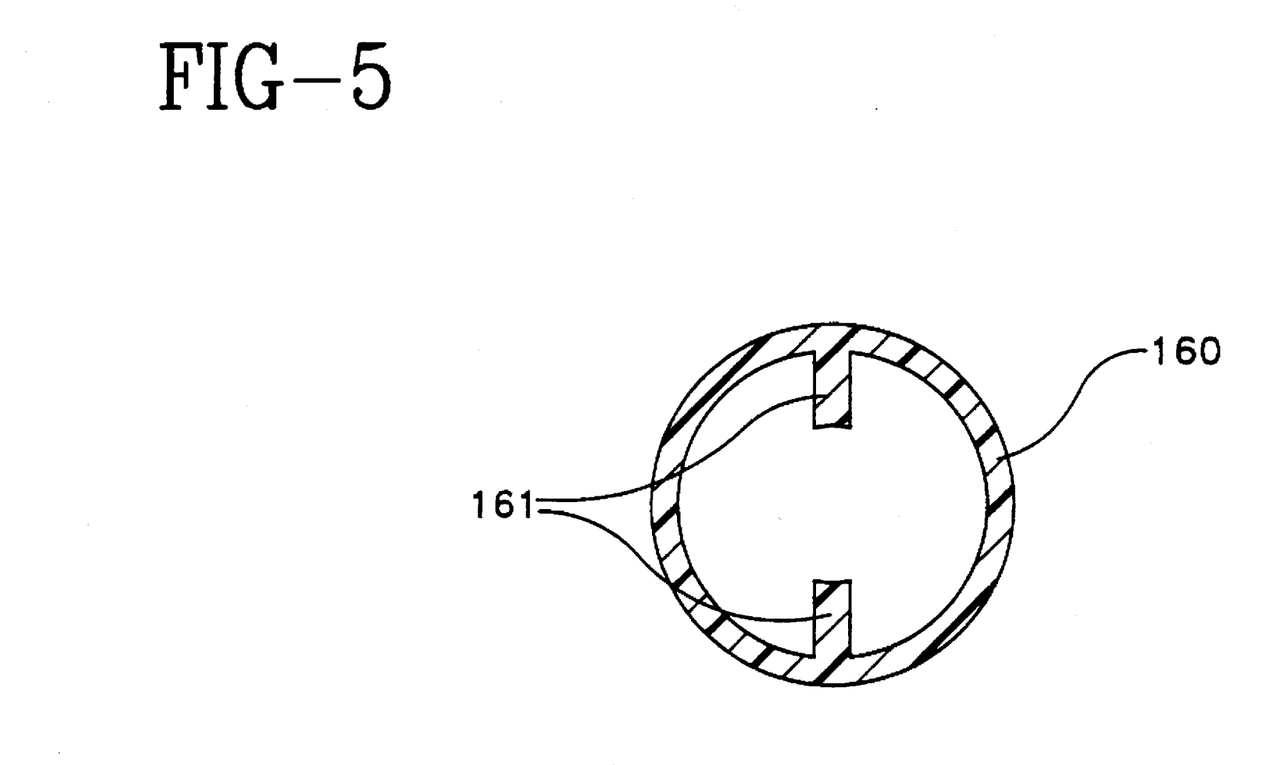
FIG. 5 is a cross-sectional view of the medication delivery pen shown in FIG. 2 along lines 5—5.

The preferred embodiment of reusable pen body assembly 100 is illustrated in detail in FIGS. 2–4. It is understood, however, that variations from this preferred embodiment may be provided, and are considered to be within the scope of the subject invention. Reusable pen body assembly 100 includes a cylindrical housing 101 having opposed proximal and distal ends 102 and 103. An array of external threads 105 extends proximally from distal end 103 for threaded engagement with threads 303 in proximal end 301 of cartridge holder assembly 300. Portions of housing 101 adjacent distal end 103 are characterized by an array of clutch teeth (not shown) molded therein. Proximal end 102 of housing 101 is characterized by a cut-out 106 formed therein for receiving a window insert 150 having a window 151 and a button 152.

Pen body assembly 100 further includes a nut 110 having opposed proximal and distal ends 111 and 112, respectively. Exterior surface regions of nut 110 between proximal and distal ends 111 and 112 define a plurality of longitudinally extending splines 113. Proximal end 111 of nut 110 is characterized by a plurality of longitudinally extending resilient fingers 114 with enlarged ends that enable snap engagement of nut 110 into other portions of pen body assembly 100 as explained further herein. Distal end 112 of nut 110 is radially enlarged to limit axial movement of nut 110 into distal end 103 of housing 101. Thus, nut 110 is axially constrained within housing 101. However, the dimensions and configurations of nut 110 and housing 101 permit free relative rotation therebetween.

Pen body assembly 100 further includes a clutch assembly having a proximal clutch 141, a distal clutch 143 and an annular spring 142 biasingly engaged therebetween. Proximal and distal clutches 141 and 143 are both configured for non-rotatable engagement over splines 113 of nut 110. Distal clutch 143 includes an array of distally facing saw teeth (not shown) dimensioned, disposed and configured for engagement with the teeth (not shown) on interior surface 108 of housing 101, such that distal clutch 143 can rotate only in one direction relative to housing 101. Proximal clutch 141 includes an array of proximally facing teeth (not shown) which are also configured for unidirectional rotation as explained further herein.

Pen body assembly 100 further includes a drive mechanism having a generally cylindrical driver 50 with opposed proximal and distal ends 451 and 452. Driver 450 is slidably inserted into housing 101 of pen body assembly 100 such that distal end 452 of driver 450 is snap fit over the enlarged ends of resilient fingers 114 at proximal end 111 of nut 110. This snap fit engagement prevents axial movement between nut 110 and driver 450, but permits free relative rotational movement within housing 101. Distal end 452 of driver 450 is also characterized by an array of saw teeth (not shown) that engage with the saw teeth on proximal clutch 141. Outer surface regions of driver 450 are characterized by splines 454 extending radially outwardly thereon and along a substantial portion of the length of driver 450.

Figure 6:
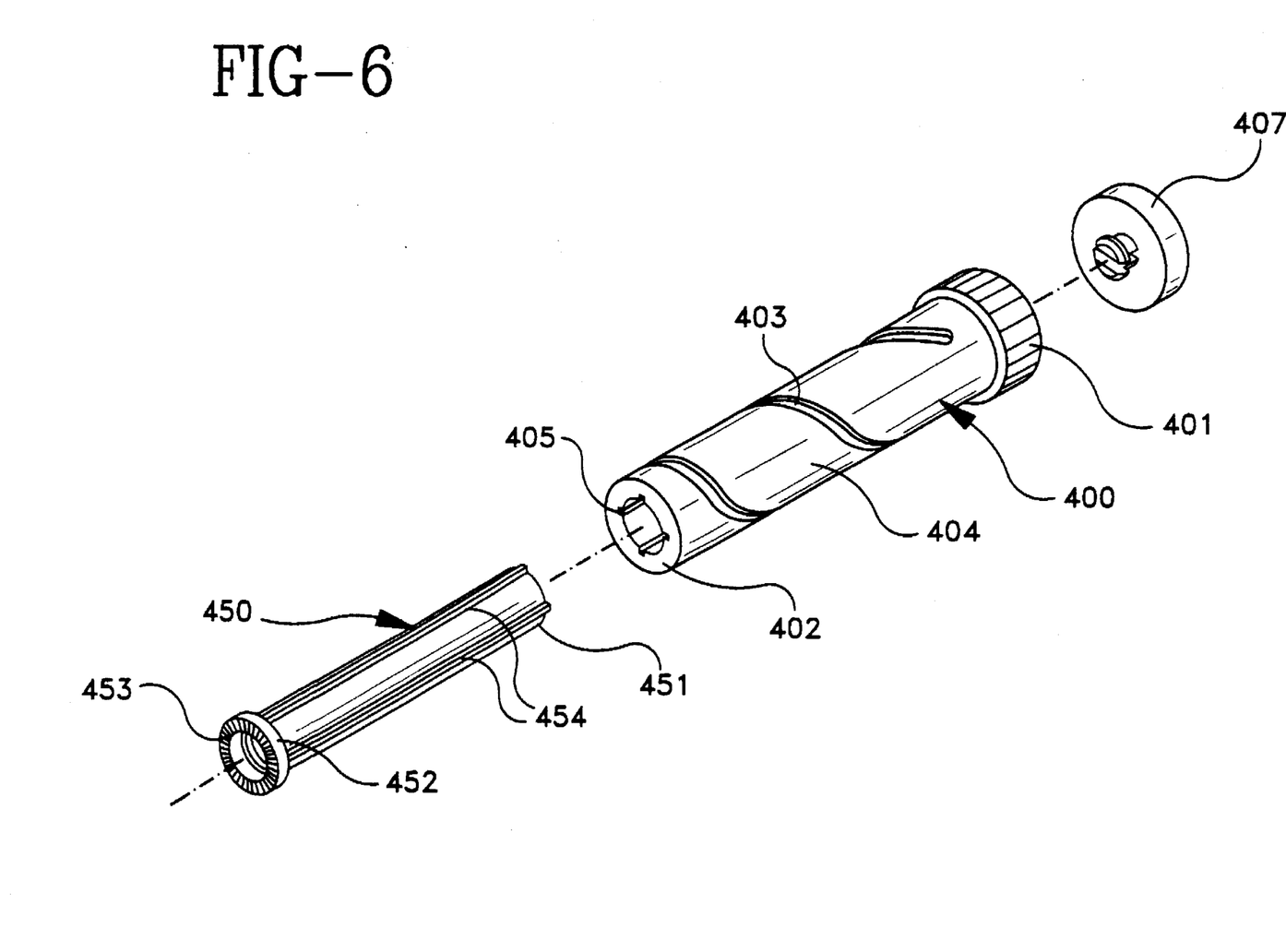
FIG. 6 is a further exploded perspective view of dose knob 400 and driver 450, shown in FIG. 2.

Pen body assembly 100 further includes a dose knob 400 which is a hollow generally cylindrical structure having opposed proximal and distal ends 401 and 402 and opposed inner and outer surfaces. As shown in FIG. 6, the inner surface is characterized by longitudinally extending grooves 405 which are disposed and dimensioned for engagement with splines 454 on driver 450. More particularly, dose knob 400 is spline mounted over driver 450 within housing 101 of pen body assembly 100. Thus, axially extending grooves 405 in dose knob 400 engage splines 454 of driver 450 to prevent relative rotation therebetween, but permitting relative axial movement. The outer surface of dose knob 400 is characterized by a helical groove 403 with dosage indicia to define dose amounts corresponding to different positions along helical groove 403. Proximal end 401 of dose knob 400 is characterized by a gnarled exterior surface to facilitate manipulation for setting a selected dose having an actuator button 407 snapped therein to permit relative rotation therebetween.

Insert 150 is snapped into engagement with cut-out 106 in the proximal end 102 of housing 101. Insert 150 includes a window 151 therethrough and button 152 on an interior face that is dimensioned and disposed to engage with helical groove 403 on dose setting knob 400. Button 152 and window 151 are disposed to also enable the dosage indicia on dose setting knob 400 to be visible through window 151 as dose knob 400 is rotated.

Pen body assembly 100 includes a lead screw 120 with opposed proximal and distal ends 121 and 122 and an array of external threads 123. External threads 123 are characterized, however, by a pair of opposed axially extending grooves 124 which extend from an enlarged head 125 at distal end 122 substantially to the proximal end 121. Threads 123 are threadably engaged in nut 110, such that proximal end 121 of lead screw 120 is within housing 101 and distal end 122 projects distally beyond housing 101. Threads 123 on lead screw 120 have exactly the same pitch and the same hand as threads 105 on distal end 103 of housing 101.

Pen body assembly 100 further includes an anti-rotation ring 160, shown in FIGS. 2–5, having a pair of tabs 161 extending therein and splines 162 on its distal surface. Each tab 161 slidable engages groove 124 on lead screw 120 to allow anti-rotation ring 160 to travel on and rotate with lead screw 120. Thus, lead screw 120 can slidably move relative to anti-rotation tabs 161, but is prevented from rotating relative to anti-rotation tabs 161.

Pen body assembly 100 is assembled by placing nut 110 into housing 101 from distal end 103. Clutch assembly 141, 142 and 143 then is mounted over splines 113 on nut 110. Driver 450 is then inserted into proximal end 102 of housing 101, and is urged sufficiently in a distal direction for snap fit engagement with nut 110. In this snapped engagement, the saw teeth of distal clutch 143 will be secured in engagement with the teeth in of housing 101, and the saw teeth of proximal clutch 141 will be engaged with the saw teeth at distal end 452 of driver 450. Spring 142 will maintain constant selected pressure between these interengaged saw teeth. Insert 156 then is positioned over dose knob 400 such that button 152 of insert 150 is engaged in the helical groove 403 in dose knob 400. The temporarily assembled insert 150 and dose knob 400 then are into housing 101. Lead screw 120 then is threaded into nut 110, and actuator button 407 is snapped into engagement with proximal end 401 of dose knob 400. Finally, anti-rotation ring 160 is slid onto lead screw 120 and a retaining ring 163 on ring 160 is rotatably attached to a receiving ring 165 at distal end 103 of pen housing 101.

Cartridge holder assembly 300, shown in detail in FIGS. 2 and 3, includes a molded housing 304 which extends from proximal end 301 to distal end 302 of cartridge holder assembly 300. Housing 304 includes a mounting cavity 305 extending inwardly from proximal end 301. Mounting cavity 305 is characterized by an array of internal threads 303 for threaded engagement with external threads 105 on distal end 103 of housing 101. A set of splines 306 are located in proximal end 301 of cartridge holder assembly 300 to receive splines 162 on anti-rotation ring 160 when cartridge holder assembly 300 is threaded onto housing 101 to prevent cartridge holder assembly 300 from rotating with respect to lead screw 120 but continue to rotate with respect to pen housing 101. However, when pen 10 is fully assembled, splines 162 are fully engaged with splines 306 so that lead screw 120 is then engaged with the remaining drive mechanism in the pen and ready for dose setting and dispensing operations.

Cartridge holder assembly 300, further includes a medication cartridge 350 securely retained in housing 304 between proximal end 301 and distal end 302. Medication cartridge 350 includes an open proximal end 351 and a distal end 352 having a pierceable elastomeric seal 353 securely mounted thereto. A cap 354 extends between housing 304 and cartridge 350 for securely and permanently holding medication cartridge 350 in housing 304. A plunger 355 is disposed in sliding fluid tight engagement in cartridge 350. As shown in FIG. 3, plunger 355 is disposed in primed contact with plunger 355 of medication cartridge 350 when fully threaded to cartridge holder assembly 300. Portions of cartridge 350 between plunger 355 and seal 353 are filled with a medication 356, such as insulin.

Needle cannula assembly 500 includes a double ended needle cannula 501 having opposed proximal and distal points 502 and 503, respectively, and a lumen extending axially therebetween. A mounting hub 504 is engaged on needle cannula 501 and is threadably engageable with cap 354 of cartridge holder assembly 300. The relative location of mounting hub 504 ensures that proximal point 502 of needle cannula 501 will pierce seal 353 when mounting hub 504 is engaged with cap 354. Needle cannula assembly 500 further includes a shield 600 removably mounted thereon for protecting against accidental needle sticks until immediately prior to use of pen 10.

As noted above, pen body assembly 100 is reusable and cartridge holder assembly 300 is disposable. More particularly, cartridge 350 in cartridge holder assembly 300 will contain a volume of medication 356 sufficient for administration of several doses. After exhaustion of the medication 356, cartridge holder assembly 300 will be threadedly disengaged from pen body assembly 100 and discarded. A new cartridge holder assembly 300 may then be mounted to the reusable pen body assembly 100.

To effect the mounting of a new cartridge holder assembly 300 to the reusable pen body assembly 100, the patient need merely advance distal end 122 of lead screw 120 into cartridge holder assembly 300 until distal end 122 of lead screw 120 engages plunger 355. Assembly continues by merely exerting axial forces on actuator button 407 and on cartridge holder assembly 300 Additionally, friction between plunger 355 and cartridge 350 and fluid forces exerted by medication 356 and seal 353 will prevent axial advancement of lead screw 120 beyond the position depicted in FIG. 3 during assembly. Additionally, the splined engagement of distal clutch 143 with nut 110 and the engagement of the teeth on distal clutch 143 with the corresponding teeth in housing 101 prevent independent rotation of nut 110 with respect to housing 101, during this initial mounting of reusable pen body assembly 100 with a new cartridge holder assembly 300. Therefore, axial forces exerted on actuator button 407 will cause housing 101 to rotate and advance towards cartridge holder assembly 300 as nut 110 rotates on threads 123 of lead screw 120.

After sufficient axial advancement, threads 105 at distal end 103 of pen body housing 101 will engage internal threads 303 at proximal end 301 of cartridge holder assembly 300. As noted above, external threads 105 at distal end 103 of housing 101 have exactly the same pitch and hand as threads 123 on lead screw 120. Hence, further axial forces exerted on actuator button 407 will cause the simultaneous threaded advancement of housing 101 along lead screw 120 and into cavity 305 at proximal end 301 of cartridge holder assembly 300. Because of the identical pitches, lead screw 120 will move proximally relative to pen body housing 101, while pen body housing 101 and cartridge holder assembly 300 are approaching their fully seated and threaded condition. When fully seated and threaded, lead screw 120 is fully engaged to the drive mechanism and can be driven by the drive mechanism when medication dispensing is desired.

The assembled reusable pen body assembly 100 and cartridge holder assembly 300 may be stored until a selected dose of medication is required. Just prior to use, a needle cannula assembly 500 may be threadedly engaged to distal end 302 of cartridge holder assembly 300. This threaded engagement will cause proximal point 502 of needle cannula 501 to pierce seal 353 and provide communication with medication 356. Shield 600 may then be removed.

A desired dose of medication 356 is then set by rotating dose knob 400 until indicia corresponding to the desired dose appears in window 151 of insert 150. The engagement of button 152 on insert 150 in helical groove 403 in dose knob 400 will cause a threaded retraction of dose knob 400 relative to housing 101 of reusable pen body assembly 100. This threaded retraction of dose knob 400 will cause a simultaneous rotation of driver 450 splined thereto. However, nut 110 will not rotate because the saw teeth on distal clutch 143 and the saw teeth on interior portions of housing 101 are locked to prevent rotation in that direction. Proximal clutch 141 is splined to nut 110, and hence also will not turn. However, saw teeth 453, shown in FIG. 6, at distal end 452 of driver 450 are shaped to allow rotation relative to proximal clutch 141 and provide an audible click for each unit of medication in the selected dose. This is helpful for visually impaired patients who may be required to set doses and administer insulin or other medication to themselves. Annular spring 142 contributes to the engagement that provides these audible clicking sounds.

When the desired dose is set, injection is achieved by merely pushing on actuator button 407. This causes dose knob 400 to turn about helix 403 relative to pen body housing 101, and driver 450 rotates through the same number of degrees. This rotation is opposite to the rotation generated by the dose setting procedure, and the rotational freedom of the clutch assembly 140 is reversed. Thus, as driver 450 turns the previously clicking proximal clutch 141 is locked to and turns with driver 450. This driving movement of proximal clutch 141 causes a corresponding rotational movement of nut 110 because of the splined engagement therebetween. Distal clutch 143 is now free to rotate against the saw teeth on housing 101, and makes an audible clicking indication during injection of medication.

Rotation of lead screw 120 is prevented by splines 306 unitary molded in cartridge holder assembly 300 mating with splines 162 on anti-rotation ring 160 engaged with lead screw 120 and causes lead screw 120 to be engaged with the drive mechanism. Therefore, as nut 110 rotates under the driving action of proximal clutch 141 and driver 450, lead screw 120 will be advanced axially into cartridge holder assembly 300. This axial advancement of lead screw 120 causes distal end 122 to urge plunger 355 distally into cartridge 350, and hence causes medication 356 to be injected through needle cannula 501. Injection will be terminated when proximal end 401 of dose knob 400 engages proximal end 102 of pen body housing 101.

Upon completion of the injection, needle cannula assembly 500 may be disengaged from cartridge holder assembly 300 and safely discarded. Cap 200 may be mounted over cartridge holder assembly 300, and pen 10 may be stored or carried in a convenient location until the next dose of medication is required. A subsequent dose of medication will be set in exactly the manner as described above. However, for such a subsequent dose, lead screw 120 and plunger 355 will be in a partly advanced position as a starting point. Dose setting and injections can be carried out until all of medication 356 has been used. Cartridge holder assembly 300 may then be threadedly disengaged from pen body assembly 100, and slidably separated from lead screw 120. The separated cartridge holder assembly may then be discarded and replaced as described above.

While the invention has been described with respect to a preferred embodiment, it is apparent that various changes can be made without departing from the scope of the invention as defined by the appended claims. In particular, the reusable pen body assembly may have other driving and/or clutch mechanisms. Additionally, different means for preventing and/or enabling rotation during the dose setting and injection phases may be provided. Similarly, other means for mounting needle cannula to the cartridge holder assembly may be provided. These various optional constructions will be apparent to those skilled in the an after having read the subject disclosure.

What is claimed is:

1. A medication delivery pen comprising:
  a cartridge holder assembly for holding a cartridge having a plunger, said cartridge holder assembly having a plurality of threads at a proximal end; and
  a pen body assembly releasably mountable on said cartridge holder assembly of said medication delivery pen for moving said plunger within said cartridge, said pen body assembly comprising:
    a plurality of threads at a distal end for threading with said plurality of threads in said cartridge holder assembly;
    a lead screw extending from the distal end for engaging the plunger in the cartridge in said cartridge holder;
    means in said pen body assembly for driving said lead screw into said cartridge to move the plunger in the distal direction;
    means in said pen body assembly for disengaging said driving means from said lead screw to permit said lead screw to automatically and easily retract into said pen body assembly as said pen body assembly approaches and is being threaded to said cartridge holder assembly; and
    means in said pen body assembly for engaging said driving means to said lead screw to prime said medication delivery pen, when said pen body assembly is fully threaded onto said cartridge holder assembly,
  wherein said means for disengagin and means for engaging include:
    an anti-rotation ring slidably mounted on said lead screw to prevent said lead screw from rotating with respect thereto, said anti-rotation ring having a spline extending in the distal direction into said cartridge holder assembly; and
    a spline located within said cartridge holder assembly for mating with said spline on said anti-rotation ring to prevent said lead screw from rotating with respect to said cartridge holder assembly and engage said lead screw to said driving means, when said pen body assembly is fully threaded onto said cartridge holder assembly.

2. A medication delivery pen according to claim 1, wherein said lead screw includes a longitudinal groove and said anti-rotation ring includes a tab that is received in said groove to prevent said lead screw from rotating with respect to said anti-rotation ring.

3. The medication delivery pen of claim 1, wherein said cartridge holder assembly further comprises a housing unitarily molded from a plastic material with said spline being a unitary portion of said housing.

4. A medication delivery pen according to claim 1, wherein:
   said plurality of threads in said pen body assembly are dimensioned and have a pitch for threaded engagement with said plurality of threads at the proximal end of said cartridge holder assembly; and
   said lead screw further comprises a proximal end disposed in said pen body assembly with an array of threads extending between the proximal end and the distal end of said lead screw and having a pitch substantially equal to said pitch of said plurality of threads in said pen body assembly.

5. The medication delivery pen of claim 1, wherein said pen body assembly further comprises dose setting means in said pen body assembly for defining specified distances of travel for said lead screw corresponding to selected doses of medication to be delivered.

6. The medication delivery pen of claim 1, further comprising a needle cannula assembly that is selectively engageable and disengageable from the distal end of said cartridge holder assembly.

7. A medication delivery pen comprising:
   a cartridge holder assembly for holding a cartridge having a plunger, said cartridge holder assembly having a plurality of threads at a proximal end; and
   a pen body assembly releasably mountable on said cartridge holder assembly of said medication delivery pen for moving said plunger within said cartridge, said pen body assembly comprising:
      a plurality of threads at a distal end for threading with said plurality of threads in said cartridge holder assembly;
      a lead screw extending from the distal end for engaging the plunger in the cartridge in said cartridge holder;
      means in said pen body assembly for driving said lead screw into said cartridge to move the plunger in the distal direction;
      means in said pen body assembly for disengaging said driving means from said lead screw to permit said lead screw to automatically and easily retract into said pen body assembly as said pen body assembly approaches and is being threaded to said cartridge holder assembly; and
      means in said pen body assembly for engaging said driving means to said lead screw to prime said medication delivery pen, when said pen body assembly is fully threaded onto said cartridge holder assembly,
   wherein said means for disengaging and means for engaging include:
      an anti-rotation ring slidably mounted on said lead screw to prevent said lead screw from rotating with respect thereto, said anti-rotation ring having a plurality of splines extending in the distal direction into said cartridge holder assembly; and
      a plurality of splines located within said cartridge holder assembly for mating with said plurality of splines on said anti-rotation ring to prevent said lead screw from rotating with respect to said cartridge holder assembly and engage said lead screw to said driving means, when said pen body assembly is fully threaded onto said cartridge holder assembly.

8. A medication delivery pen comprising:
   a medication-containing cartridge holder assembly including:
      an open proximal end having an array of threads,
      a cartridge having a pierceably sealed distal end, and
      a plunger in sliding fluid tight engagement within said cartridge at a location distally of said array of threads; and
   a pen body assembly releasably mountable on said medication-containing cartridge holder assembly of said medication delivery pen for moving said plunger within said cartridge, said pen body assembly having:
      a housing surrounding said pen body assembly and having opposed proximal and distal ends, said distal end having an array of threads dimensioned and having a pitch for threaded engagement with said array of threads at said proximal end of said medication-containing cartridge holder assembly,
      a lead screw having a proximal end disposed in said housing, a distal end projecting beyond said distal end of said housing for selective engagement with said plunger, and an array of threads extending between said proximal and distal ends of said lead screw and having a pitch substantially equal to said pitch of said array of threads at said distal end of said pen body assembly,
      driver means in said pen body assembly for moving said lead screw distally into said pen body assembly by preselected amounts,
      dose setting means in said pen body assembly for defining specified distances of distal travel for said lead screw corresponding to selected doses of medication to be delivered and causing said driver means to move said lead screw distally a preselected amount corresponding to a selected dose, and
      means in said pen body assembly for engaging said lead screw and said driver means and preventing said lead screw from moving in a proximal direction into said pen body assembly, when said pen body assembly is fully threaded onto said medication-containing cartridge holder assembly.

9. A medication delivery pen according to claim 8, wherein said means for engaging said lead screw and said driver means and preventing said lead screw from moving in a proximal direction into said pen body assembly include:
   an anti-rotation ring slidably mounted on said lead screw to prevent said lead screw from rotating with respect thereto, said anti-rotation ring having a spline extending in the distal direction into said medication-containing cartridge holder assembly; and
   a spline located within said medication-containing cartridge holder assembly for mating with said spline on said anti-rotation ring to prevent said lead screw from rotating with respect to said medication-containing cartridge holder assembly and engage said lead screw to said driver means, when said pen body assembly is fully threaded onto said medication-containing cartridge holder assembly.

* * * * *